United States Patent
Kumaran et al.

(10) Patent No.: US 9,804,113 B2
(45) Date of Patent: Oct. 31, 2017

(54) SOIL MOISTURE SENSOR

(71) Applicant: Fiskars Oyj Abp, Helsinki (FI)

(72) Inventors: Hari Hara Kumaran, Tamil Nadu (IN); Vibha Tomar, Karnataka (IN)

(73) Assignee: Fiskars Oyj Abp, Helsinki (FI)

(*) Notice: Subject to any disclaimer, the term of this patent is extended or adjusted under 35 U.S.C. 154(b) by 6 days.

(21) Appl. No.: 14/715,352

(22) Filed: May 18, 2015

(65) Prior Publication Data
US 2015/0330932 A1 Nov. 19, 2015

(30) Foreign Application Priority Data
May 19, 2014 (IN) .......................... 2485/CHE/2014

(51) Int. Cl.
*G01N 27/22* (2006.01)
*A01G 25/16* (2006.01)

(52) U.S. Cl.
CPC ......... *G01N 27/223* (2013.01); *A01G 25/167* (2013.01); *G01N 27/221* (2013.01)

(58) Field of Classification Search
CPC .. G01N 27/223; G01N 27/221; G01N 27/226; G01N 27/225; G01N 33/246; A01G 25/167
See application file for complete search history.

(56) References Cited

U.S. PATENT DOCUMENTS

| | | | | |
|---|---|---|---|---|
| 4,683,904 A * | 8/1987 | Iltis | ..................... | A01G 25/167 137/624.11 |
| 4,850,386 A * | 7/1989 | Bireley | ................ | G01N 27/223 137/78.3 |
| 5,207,380 A * | 5/1993 | Harryman | ............ | A01G 25/165 137/78.3 |
| 5,445,178 A * | 8/1995 | Feuer | .................... | A01G 25/167 137/1 |
| 5,546,974 A * | 8/1996 | Bireley | ................ | A01G 25/167 137/624.12 |
| 5,859,536 A * | 1/1999 | Stockton | ............ | G01R 27/2623 239/64 |
| 6,798,215 B2 * | 9/2004 | DeHart | .................. | G01N 22/04 324/640 |
| 6,975,245 B1 * | 12/2005 | Slater | .................... | A01G 25/167 239/63 |
| 7,474,105 B2 * | 1/2009 | McDermid | .......... | G01N 27/223 324/664 |

(Continued)

FOREIGN PATENT DOCUMENTS

GB   2 344 422 B   6/2000

OTHER PUBLICATIONS

International Search Report and Written Opinion, PCT/IB2015/053663, Fiskars Oyj Abp (dated Aug. 10, 2015).

(Continued)

*Primary Examiner* — Jermele M Hollington
*Assistant Examiner* — Suresh K Rajaputra
(74) *Attorney, Agent, or Firm* — Foley & Lardner LLP

(57) ABSTRACT

A soil moisture sensor includes a capacitive probe configured to be inserted into soil, a series RLC circuit electrically coupled to the capacitive probe, a microcontroller configured to determine the capacitance value of the soil and determine the moisture content of the soil from the capacitance value of the soil.

19 Claims, 4 Drawing Sheets

(56) References Cited

U.S. PATENT DOCUMENTS

| | | | | |
|---|---|---|---|---|
| 7,836,910 | B2* | 11/2010 | Dresselhaus | G01N 27/223 137/78.3 |
| 8,104,498 | B2* | 1/2012 | Dresselhaus | G01N 27/223 137/78.3 |
| 8,671,969 | B2* | 3/2014 | Dresselhaus | G01N 27/223 137/78.3 |
| 8,885,558 | B2 | 11/2014 | Jacobs et al. | |
| 2007/0068266 | A1* | 3/2007 | Fujimori | B60C 23/0408 73/724 |
| 2008/0199359 | A1* | 8/2008 | Davis | G01D 5/2405 422/82.01 |
| 2009/0134889 | A1* | 5/2009 | Gunsay | A01G 25/167 324/694 |
| 2009/0302870 | A1* | 12/2009 | Paterson | A01G 25/167 324/670 |
| 2009/0308155 | A1* | 12/2009 | Zhang | G01N 27/223 73/335.02 |
| 2010/0277185 | A1* | 11/2010 | Hughes | G01N 33/246 324/664 |
| 2013/0255783 | A1* | 10/2013 | Runge | A01G 25/167 137/1 |

OTHER PUBLICATIONS

International Preliminary Report on Patentability, PCT/IB2015/001427, Fiskars Oyj Abp, 14 pages (dated Nov. 17, 2016).

* cited by examiner

SOIL MOISTURE SENSOR

CROSS-REFERENCE TO RELATED PATENT APPLICATIONS

This application claims the benefit of Indian Application No. 2485/CHE/2014, filed May 19, 2014, which is incorporated herein by reference in its entirety.

BACKGROUND

The application relates generally to moisture sensors and in particular to moisture sensors for measuring water content in soil.

It is often desirable to detect the moisture content of a granular, particulate, fine or powdery medium. For example, in agriculture, it is often desirable to detect the moisture content of the soil in a region, so that irrigation or drainage systems can be controlled in accordance with the sensed moisture content. Soil moisture detection is also desirable for other purposes, e.g., for monitoring and evaluating the soil condition in construction sites, landscaped sites, mining operations, forest areas, flood control areas, or bio-remediation areas, such as areas in which liquid or other contaminant has spilled.

The ability to determine the moisture content of granular, particulate, fine or powdery media is also important in many other applications, such as cement or plaster making systems, gravel or brick processing systems, mined material moving or processing systems and food processing or handling systems, to name just a few. Another application for moisture content monitoring relates to the monitoring of the moisture content of certain water absorbing substrates, such as mushroom substrates, or other agricultural or laboratory substrates. As the demand for agricultural products increases and as the demand for higher quality products made from granular, particulate, fine or powdery media, or made with a moisture absorbing media increases, so does the demand for high quality moisture detection systems. Accurate moisture detection systems can dramatically increase the ability to meet the increasing market demands for these products. In addition, accurate moisture detection systems can increase the manufacturing efficiency and quality of such products.

For low dielectric media (such as soil), it has been recognized that moisture content affects the overall dielectric constant of such media to a detectable degree. For example, water has a relatively high dielectric constant of 80, while dry soil typically has a much lower dielectric constant of approximately 5 or 6. The water content in soil is, thus, generally a major contributor to the overall dielectric constant of the soil. An increase in the moisture content of soil will generally result in an increase in the dielectric constant of the soil. The same is typically true with many other low dielectric granular, particulate, fine or powder substances or media.

Accordingly, moisture sensors have been developed for reacting to the dielectric property of the medium being monitored. Moisture sensors of contemporary design typically employ a parallel plate capacitor configured to be immersed or embedded in the medium so that a portion of the medium becomes embedded between the parallel plates and functions as a dielectric between the plates. The capacitance provided by such a capacitor is used as part of an RC oscillator circuit having an oscillation frequency which varies with changes in the dielectric property of the small portion of the medium between the plates. The frequency of the oscillator circuit is used as an indicator of the moisture content of the medium.

The methods used to derive the capacitance from the frequency oscillator circuit in the prior art typically comprise either single frequency complex impedance calculation or sweeping the frequency to find the resonant point. In all the cases the frequency required for determining capacitance is very high in terms of MHz (e.g., 10 MHz). The high frequency requirement requires complex circuit design and/or costly components to implement.

SUMMARY OF THE INVENTION

One embodiment of the invention relates to a soil moisture sensor including a capacitive probe configured to be inserted into soil, a series RLC circuit electrically coupled to the capacitive probe, a microcontroller configured to determine the capacitance value of the soil and determine the moisture content of the soil from the capacitance value of the soil.

Another embodiment of the invention relates to a soil moisture sensor including a capacitive probe comprising two electrodes configured to be inserted into soil, a series RLC circuit electrically coupled to the capacitive probe, a microcontroller comprising a pulse-width modulated signal generator and an analog-to-digital converter, and a current-to-voltage converter electrically coupled to the microprocessor. The pulse-width modulated signal generator provides a drive signal to the series RLC circuit and the drive signal frequency is selected with reference to a resonance curve of the series RLC circuit. The series RLC circuit provides an input signal to the capacitive probe. An output signal dependent on the capacitance of the soil between the two electrodes is induced by the input signal and the output signal is provided to the current-to-voltage converter. The current-to-voltage converter converts the output signal to a proportional output voltage and the proportional output voltage is provided to the analog-to-digital converter. The analog-to-digital converter converts the proportional output voltage to a digital signal. The microcontroller determines the capacitance value of the soil based on the digital signal. The microcontroller determines the moisture content of the soil in view of the capacitance value of the soil and the dielectric constant of the soil.

DETAILED DESCRIPTION

Figure 1:
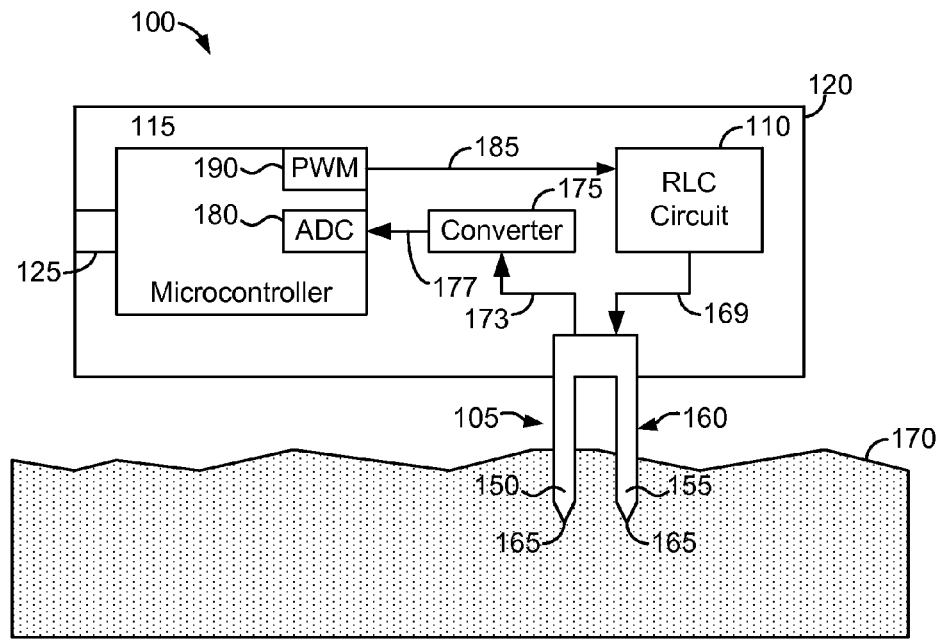
FIG. 1 is a schematic diagram of one embodiment of a soil moisture sensor having an RLC circuit.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to a person of ordinary skill in the art to which this disclosure pertains.

Figure 2:
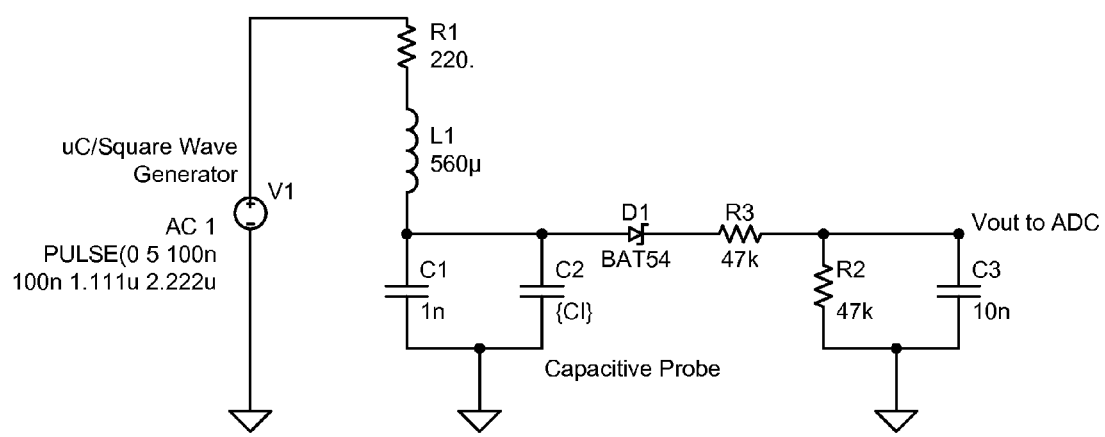
FIG. 2 is an exemplary circuit diagram of a circuit for implementing the soil moisture sensor of FIG. 1.

Referring to FIGS. 1 and 2, an embodiment of a soil moisture sensing system 100 in accordance with the disclosure is depicted. The soil moisture sensing system 100 comprises a capacitive probe 105, a series RLC circuit 110, and a microcontroller 115. In one embodiment, the capacitive probe 105, RLC circuit 110, and microcontroller 115 are integrated into a single device to form a portable, handheld sensor device 120 that is capable of both sensing and processing soil moisture information. In this embodiment, the probe 105, RLC circuit 110, and microcontroller 115 electronics may be implemented in any suitable manner, such as in one or more integrated circuit components. The components may be provided in a suitable housing. Various input/output (I/O) ports 125 may be provided on the housing for power and/or data transfer (e.g., USB) to/from the device.

Figure 3:
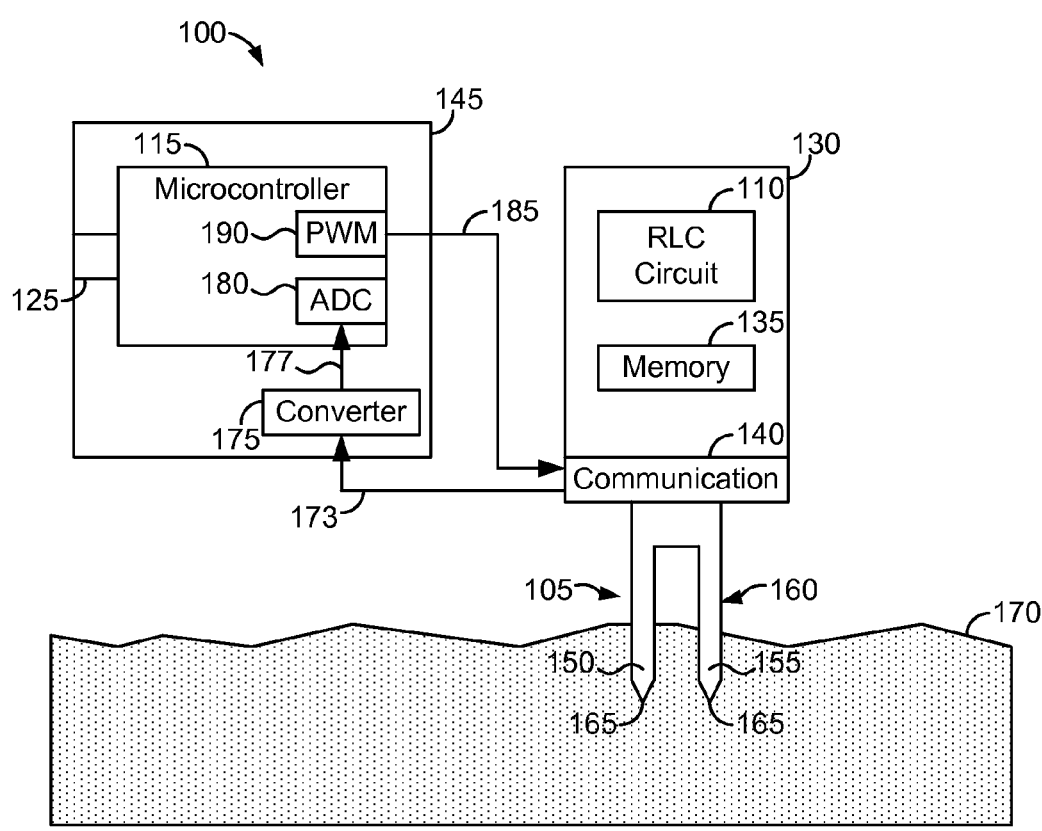
FIG. 3 is a schematic diagram of another embodiment of a soil moisture sensor having an RLC circuit.

Referring to FIG. 3, as an alternative to integrating the probe 105, RLC circuit 110, and microcontroller 115 into a single unit (e.g., device 120), the components may be distributed between separate components. For example, the capacitive probe 105 and RLC circuit 110 may be incorporated into a portable unit 130 which is intended to be transported to locations and used to collect data. The portable unit 130 may include appropriate devices for storing and/or transferring sensor data, such as memory devices 135 and/or communication devices 140. The computing devices, such as the microcontroller 115, which are used to process the data in order to derive the relevant characteristics of the tested material, such as moisture content and the like, may be implemented as a separate processing unit 145 which can be located remotely from the portable unit 130 portion of the system 100.

In a distributed system, the electronics used to generate the drive signal for the RLC tank circuit 110 are incorporated into the components and circuitry used to implement the RLC tank circuit 110 and/or capacitive probe 105. Data transfer between the portable unit 130 and the processing unit 145 may occur in any suitable manner. For example, data transfer may occur via a wired connection between the portable unit 130 and the processing unit 145 using any suitable connection type and data transfer protocol, including USB. Data transfer may also occur wirelessly between the portable unit 130 and processing unit 145. To this end, the portable unit and processing unit may be equipped with communication equipment, such as transmitters, receivers, and/or transceivers. Communication may be implemented using radio frequency (RF) transmissions or other suitable type of transmission or signal carrier (e.g., WiFi, Bluetooth®, or other appropriate wireless communication).

The capacitive probe 105 include strips of conductive material, such as metal, that are spaced apart from each other to serve as the plates, or electrodes 150, 155 of a parallel plate capacitor 160. The electrodes 150, 155 may be formed of stainless steel which is durable and resistant to corrosion although any suitable material may be used. The electrodes 150, 155 may be provided in a configuration that enables the electrodes 150, 155 to be inserted into the material, (e.g., soil) to be tested for moisture content. To this end, the electrodes 150, 155 may have pointed tips 165 to facilitate the insertion of the electrode ends into soil and similar types of materials. Alternatively, the capacitive strips may be provided on one or more substrates which provide the shape and structure of the electrodes 150, 155 for insertion into soil.

During operation, an input signal 169 is fed to the electrode 150 which induces an output current in the electrode 155 dependent on the capacitance between the two electrodes 150, 155. The output current is used to derive the capacitance value of the soil 170. The capacitance between the electrodes 150, 155 depends upon the dielectric constant as well as the moisture content of the soil 170 between the probes. The dielectric constant of the soil 170 is known or can be determined which enables the capacitance value to be correlated to a moisture content value for the soil. The dielectric constant of the soil 170 may be input to the microcontroller 115 via a user input device (e.g., touch screen, keyboard, keypad, mouse, etc.) or otherwise communicated to the microcontroller 115 (e.g., via I/O port 125) so that the determinations made by the microcontroller are done in view of the dielectric constant of the specific soil sample being tested with the system 100. The user input device may be integrated into the device 120 or the processing unit 145 or be separate from the device 120 or the processing unit 145.

In the system of FIG. 1, the output current 173 of the capacitive probe 105 is fed to a current-to-voltage converter 175 which converts the output current into a proportional output voltage 177. The output voltage is then provided to the microcontroller 115 for processing to determine the capacitance value for the soil 170. In some embodiments, the current-to-voltage converter 175 is a component of the microcontroller 115. In some embodiments, the output voltage is provided as an input to an analog-to-digital (ADC) converter 180 incorporated into the microcontroller 115 which converts the analog output voltage to a digital signal indicative of the capacitance defected by the probe 105.

Figure 4:
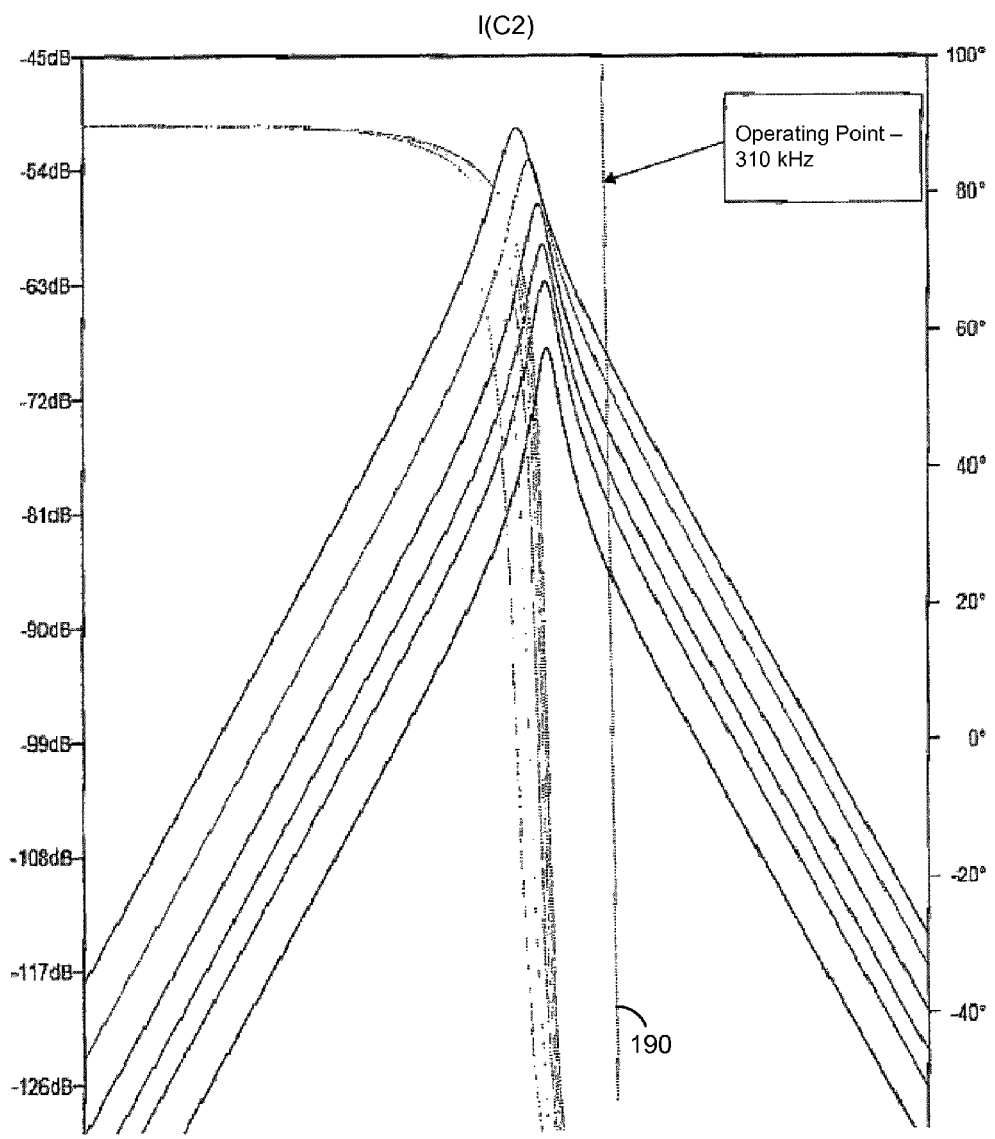
FIG. 4 is a graph of the resonance curves of the RLC circuit of the sensor of FIG. 1.

The current used to drive the capacitive probe 105 is provided by the series RLC circuit 110. The RLC tank circuit 110 receives a drive signal 185 having a predetermined frequency from the microcontroller 115. In some embodiments, the drive signal 185 is provided as a square-wave signal. As can be seen in FIG. 1, the microcontroller may include a pulse-width modulated (PWM) signal generator 190 for generating the square-wave signal 185 for the RLC circuit 110. The frequency of the signal 185 applied to the RLC circuit 110 is selected with reference to the resonance curve of the RLC circuit 110. FIG. 4 depicts a graph of a resonance curve of an RLC circuit 110 according to an embodiment of the disclosure. As can be seen in FIG. 4, the frequency of the signal applied to the RLC circuit 110 is selected such that it falls on the falling edge (line 195) of the resonance curve.

The resonance curve of the RLC circuit 110 depends on the specifications of the circuit components (e.g., register, inductor, and capacitor) used to implement the circuit as well as the capacitance between the probes which may vary based on the properties of the soil 170. As a result, the RLC circuit 110 may have multiple different resonance curves due to the soil capacitance variation. The frequency of the drive signal 185 is selected such that it falls on the falling edge of all of the possible resonance curves which are due to the soil capacitance variation. For an embodiment of the RLC circuit 110 of FIG. 1 having a resonance curve as depicted in FIG. 4, the drive signal 185 has a frequency of 310 kHz which falls on the falling edge of each of the possible resonance curves for the RLC circuit 110.

Figure 5:
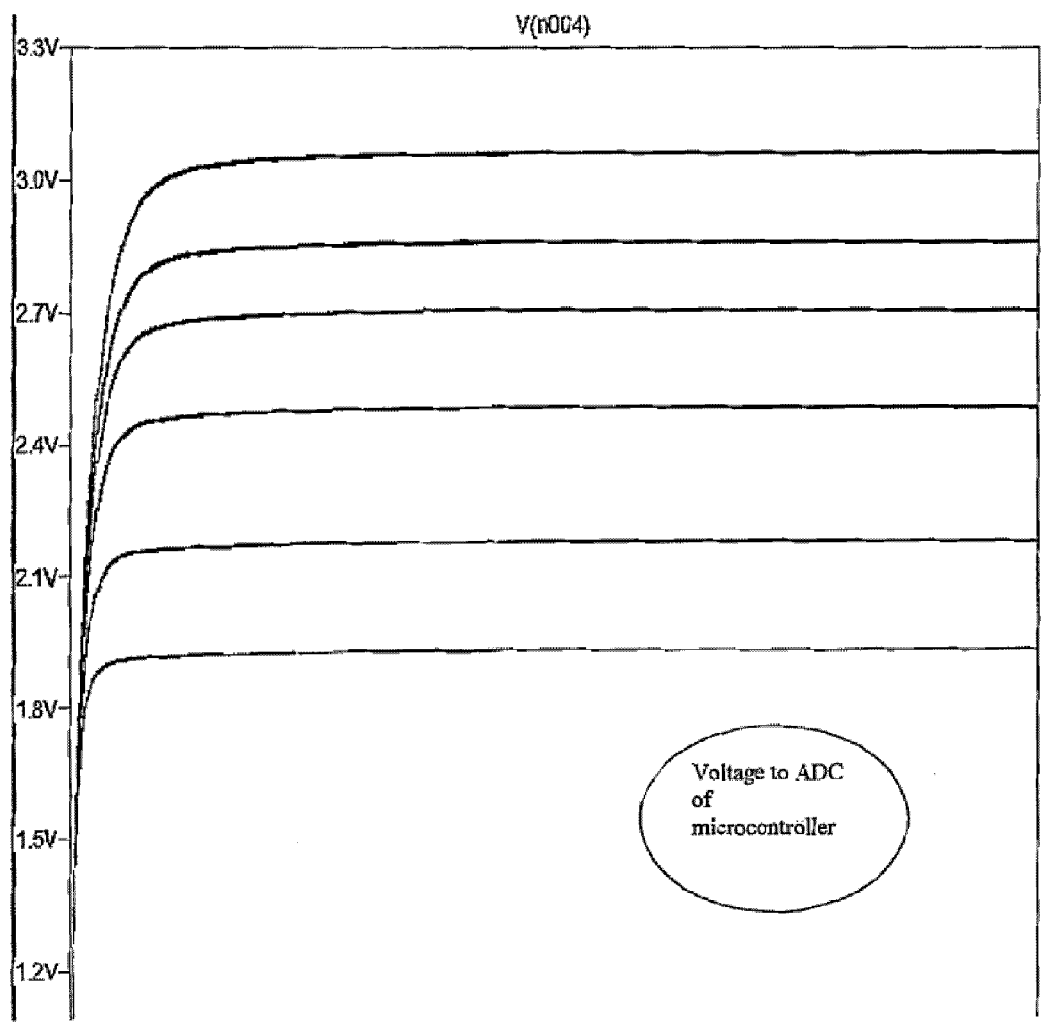
FIG. 5 is a graph of the ADC voltages based on the voltage level of the capacitor probe of the sensor of FIG. 1.

FIG. 5 depicts the voltage output by the ADC 180 based on the voltage level received from the capacitive probe 105.

As noted above, the components used to process the data from the capacitor electrodes 150, 155 may be provided in the same device or in a separate device from the probe 105. Therefore, the current data or values indicative of the output current 173 may be stored and transferred at a later time or communicated, e.g., through a wired or wireless connection, for processing by the processing devices, such as the ADC 180.

The frequency of the drive signal 185 employed for driving the RLC circuit 110 may be approximately 100-300 kHz (e.g., between 50 kHz and 500 kHz) which is lower than the frequency of the output signal resulting from such sinusoidal oscillator (e.g., 1 MHz-30 MHz). Because the current circulating through the RLC tank circuit 110 is used to drive the capacitance, the gain of the sensor can easily be adjusted by changing the value of the resistance R to achieve a better dynamic range for ADC measurement. In addition, by adding the known capacitor value of the RLC circuit 110 across the capacitive probe 105, the frequency required for measurement can be reduced. This in turn reduces the complexity of the circuit layout and the cost of the circuit used for generating the signal used for measurement. Complexity and costs are also reduced by combining resonance & circulating current measurement relative to measuring either high frequency or precise voltage attenuation and phase shift of the signal which are the part of existing techniques.

In some embodiments, the microcontroller can include a processor and memory device. Processor can be implemented as a general purpose processor, an application specific integrated circuit (ASIC), one or more field programmable gate arrays (FPGAs), a group of processing components, or other suitable electronic processing components. Memory device (e.g., memory, memory unit, storage device, etc.) is one or more devices (e.g., RAM, ROM, Flash memory, hard disk storage, etc.) for storing data and/or computer code for completing or facilitating the various processes, layers and modules described in the present application. Memory device may be or include volatile memory or non-volatile memory. Memory device may include database components, object code components, script components, or any other type of information structure for supporting the various activities and information structures described in the present application. According to an exemplary embodiment, memory device is communicably connected to processor via processing circuit and includes computer code for executing (e.g., by processing circuit and/or processor) one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges or geometric relationships provided. Accordingly, these terms should be interpreted as indicating that insubstantial or inconsequential modifications or alterations of the subject matter described and claimed are considered to be within the scope of the invention as recited in the appended claims.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A soil moisture sensor, comprising:
   a capacitive probe configured to be inserted into soil;
   a series RLC circuit electrically coupled to the capacitive probe; and
   a microcontroller configured to
      provide a drive signal having a predetermined drive signal frequency to the series RLC circuit,
      receive an output signal including one of an output voltage or an output current from the capacitive probe,
      determine the capacitance value of the soil based at least in part on the received output signal, and
      determine the moisture content of the soil based on the determined capacitance value.

2. The soil moisture sensor of claim 1, wherein the capacitive probe comprises two electrodes.

3. The soil moisture sensor of claim 2, wherein each electrode comprises a pointed tip configured for insertion into soil.

4. The soil moisture sensor of claim 2, wherein the two electrodes form a parallel plate capacitor.

5. The soil moisture sensor of claim 1, wherein the drive signal frequency is selected with reference to a resonance curve of the series RLC circuit.

6. The soil moisture sensor of claim 1, where the drive signal frequency is selected to fall on the falling edge of the resonance curve of the series RLC circuit.

7. The soil moisture sensor of claim 1, wherein the drive signal frequency is less than 1 MHz.

8. The soil moisture sensor of claim 1, wherein the drive signal frequency is between 50 kHz and 500 kHz.

9. The soil moisture sensor of claim 1, wherein the drive signal frequency is between 100 kHz and 300 kHz.

10. The soil moisture sensor of claim 1, wherein the microcontroller comprises a pulse-width modulated signal generator that provides the drive signal to the series RLC circuit.

11. The soil moisture sensor of claim 1, wherein the series RLC circuit provides an input signal to the capacitive probe.

12. The soil moisture sensor of claim 1, wherein the output signal is dependent on the capacitance of the soil between the two electrodes.

13. The soil moisture sensor of claim 1, wherein the microcontroller comprises an analog-to-digital converter, configured to receive the output signal and convert the output signal to a proportional output voltage, and
wherein the microcontroller determines the capacitance value of the soil based on the proportional output voltage.

14. The soil moisture sensor of claim 1, wherein the capacitive probe, the series RLC circuit, and the microcontroller are located in a single unit.

15. The soil moisture sensor of claim 1, wherein the capacitive probe and the series RLC circuit are located in a portable unit and the microcontroller is located in a processing unit.

16. The soil moisture sensor of claim 15, wherein the portable unit and the processing unit are configured to communicate wirelessly.

17. The soil moisture sensor of claim 15, wherein the portable unit and the processing unit are configured to communicate via a wired connection.

18. A soil moisture sensor, comprising:
a capacitive probe comprising two electrodes configured to be inserted into soil and to provide an output signal dependent on the capacitance of the soil between the two electrodes;
a series RLC circuit electrically coupled to, and providing an input signal to the capacitive probe to induce the output signal;
a current-to-voltage converter configured to receive the output signal, and convert the output signal to a proportional output voltage; and
a microcontroller comprising
a pulse-width modulated signal generator configured to provide a drive signal having a predetermined drive signal frequency to the series RLC circuit, the predetermined drive signal frequency is selected with reference to a resonance curve of the series RLC circuit, and
an analog-to-digital converter configured to receive the proportional output voltage, and convert the proportional output voltage to a digital signal,
the microcontroller configured to determine a capacitance value of the soil based on the digital signal, and to determine the moisture content of the soil in view of the capacitance value of the soil and a dielectric constant of the soil.

19. The soil moisture sensor of claim 18, wherein the capacitive probe, the series RLC circuit, the microcontroller, and the current-to-voltage converter are located in a single unit.

* * * * *